(12) United States Patent
Ramzan et al.

(10) Patent No.: US 10,309,909 B2
(45) Date of Patent: Jun. 4, 2019

(54) DIELECTRIC CONSTANT DETECTION METHOD AND DEVICE USING ANOMALOUS PHASE DISPERSION

(71) Applicant: United Arab Emirates University, Al Ain (AE)

(72) Inventors: Rashad Ramzan, Al Ain (AE); Omar Farooq Sidiqui, Madinah (SA); Azam Beg, Al Ain (AE); Omar Ramahi, Waterloo (CA)

(73) Assignee: UNITED ARAB EMIRATES UNIVERSITY, Al Ain (AE)

( * ) Notice: Subject to any disclaimer, the term of this patent is extended or adjusted under 35 U.S.C. 154(b) by 191 days.

(21) Appl. No.: 14/936,738

(22) Filed: Nov. 10, 2015

(65) Prior Publication Data

US 2017/0131334 A1  May 11, 2017

(51) Int. Cl.
  *G01R 27/26* (2006.01)
  *G01N 22/00* (2006.01)

(52) U.S. Cl.
  CPC .................................... *G01N 22/00* (2013.01)

(58) Field of Classification Search
  None
  See application file for complete search history.

(56) References Cited

U.S. PATENT DOCUMENTS

| | | | | |
|---|---|---|---|---|
| 5,994,906 A | * | 11/1999 | Morgan | F15B 15/2869 324/633 |
| 2003/0087802 A1 | * | 5/2003 | Urry | B63G 8/34 530/300 |
| 2005/0267700 A1 | * | 12/2005 | Gamache | G01N 27/028 702/65 |

OTHER PUBLICATIONS

Rashad Ramzan in IEEE Transactions on Microwave Theory and Techniques Sep. 2016, 11 pages.*
Omar Siddiqui in a Non-Invasive Phase Sensor for Permittivity and Moisture Estimation Based on Anomalous Dispersion, Published: Jun. 27, 2016, 9 page.*
David D. Smith in Cancellation of photoinduced absorption in metal nanoparticle composites through a counterintuitive consequence of local field effects, vol. 14, No. 7/Jul. 1997/J. Opt. Soc. Am. B, pp. 1625-1631.*

* cited by examiner

*Primary Examiner* — Tung S Lau
(74) *Attorney, Agent, or Firm* — Hayes Soloway PC

(57) ABSTRACT

There is provided a dielectric constant analyzer device adapted to determine a dielectric property associated with a substrate material by measuring transmission and reflection parameters for a transmission line connected to said substrate material over a specified frequency range; determining a transmission phase response based on the transmission and reflection parameters; determining an anomalous phase slope characterized by a double slope reversals based on the transmission phase response; determining a resonance frequency based on a centre point of the anomalous phase slope reversals, where the center point corresponds to an anomalous phase at the resonance frequency; and determining the dielectric constant based on the resonance frequency, the anomalous phase at the resonance frequency and the anomalous phase slope. There is also provided a method and a microcomputer for doing the same.

18 Claims, 16 Drawing Sheets

(a) Reconstructed Amplitude Response

ANALYZER DEVICE

Figure 15

MICROCOMPUTER

Figure 16

DIELECTRIC CONSTANT DETECTION METHOD AND DEVICE USING ANOMALOUS PHASE DISPERSION

FIELD OF THE INVENTION

The present invention generally relates to resonator-based dielectric constant detection methods and systems, and more particularly to a resonator-based method, analyzer device and a microcomputer for determining the dielectric constant of a material.

BACKGROUND OF THE INVENTION

The dielectric constant, also called relative permittivity ($\varepsilon_r$), is the factor by which the electric field between the charges is decreased relative to vacuum. The relative permittivity of vacuum is equal to 1. The relative permittivity is a complex quantity. The imaginary part corresponds to a phase shift of the polarization density (P) relative to the electric field (E) and leads to the attenuation of electromagnetic waves passing through the medium.

The precise measurement of dielectric constant of the material is needed to design all the engineering products which utilized the dielectric materials. Dielectrics are introduced in capacitors to increase the capacitance. Dielectrics are also used in transmission lines like in coaxial cables. Polyethylene is a popular material that is used in between the center conductor and outside shield in coaxial cables. Dielectric materials are also placed inside waveguides to form filters and enhance the cut-off frequencies of different propagation modes. Optical fibers are prime examples of dielectric waveguides. The relative permittivity of dielectric materials changes with temperature, humidity, and pressure. Different types of sensors can be constructed to detect changes in capacitance caused by changes in the relative permittivity.

The complex dielectric constant (or the relative permittivity) of a dielectric material has an imaginary part and a real part and can be expressed as $\varepsilon_r(1+j \tan \delta)$ where the loss tangent is the ratio of the imaginary part to the real part. There are multitude of the methods and procedure available to measure the static dielectric constant (at Zero frequency) and at different frequencies as well. There are wideband and narrowband methods. The traditional wideband methods scan a large frequency band and hence require extensive measurement setups which are expensive, hard to calibrate and maintain. The traditional resonator based (narrowband) methods require the determination of the complex dielectric constant by measuring the resonance frequency and the resonance bandwidth from the magnitude (amplitude) spectrum of the microwave device that contains the dielectric sample. The traditional wideband methods require the measurement of both the magnitude and the phase for determining the dielectric constant. Hence they are more complex and expensive. Furthermore, accurate calibration of the measurement equipment is needed both for the measurement of magnitude and phase to measure the true value of the absolute magnitude and absolute phase.

SUMMARY OF THE INVENTION

The dielectric detection method of the present invention use resonator-based microwave detection to determine the dielectric constant of a material. The method and the network analyzer device used in the present invention are adapted to extract the dielectric constant (both real and imaginary part) based only on the measurement of the slope of the phase. This is achieved by detecting the anomalous phase dispersion region and then determining the resonance frequency by determining the center frequency of the anomalous phase dispersion region. Thereafter, the resonant bandwidth is extracted from the slope of the anomalous dispersion region. The real part of the complex dielectric constant is extracted from the information of the resonance frequency. The imaginary part is extracted by the additional measurement of the slope of the anomalous phase. The proposed method with the network analyzer device simplifies the extraction process and the measurement setup at the same time. The extraction method utilizes a microwave resonator circuit comprising a stub and a stripline to connect the analyzer (also called printed anomalous dispersive circuit). The measurement at different frequencies is achieved by changing the length of the stub. The material whose complex permittivity is to be extracted is placed as a substrate for the printed anomalous dispersive circuit. The proposed method is simple, fast and hence of low cost. The proposed method and the associated network analyzer device are adapted to measure the dielectric constant of any solid material and can be extended readily to liquids.

The anomalous phase dispersion is a well-known phenomenon among the physics and electromagnetic researchers. This dispersion regime consists of frequencies for which the transmission phase exhibits a slope which is opposite to what is normally observed. A comparative plot of the normally observed transmission phase across a medium and the anomalously dispersive phase is given FIG. 1. The anomalous dispersion region is characterized by a sudden change in slope in the vicinity of the resonance. Since dispersion is strictly frequency dependent, this unusual phase relation in the natural dielectrics occurs only in narrow frequency bands that are centered at atomic resonances (terra hertz frequencies). As dictated by the Kramers-Kronig relationships, the anomalous dispersion should be accompanied by a strongly attenuated amplitude response across the medium. The time domain interpretation of the anomalous dispersion is even more interesting. Due to the reversal of the phase curve, the group velocity in the region of anomalous dispersion becomes negative. Hence superluminal propagation of spectrally confined Gaussian pulses has been demonstrated is previous studies. To exploit the usefulness of the anomalous dispersion in the microwave or millimeter frequencies (where most of the devices operate), passive and active resonator circuits and metamaterials have been proposed in the industry. Some of the potential applications of the anomalous dispersion are super-luminal interconnects, dispersion compensated transmission lines, wideband devices, and squint-less antenna arrays.

This invention exploits the distinctive phase characteristics of the anomalous dispersion region. Particularly, it is suggested that the complex permittivity of a dielectric medium undergoing the anomalous dispersion can be extracted by measuring the transmission phase spectrum.

The complete parametric retrieval from phase characteristics can be conducted from the exploitation of the Kramer-Kronig relations which relates the phase and magnitude of the transmission coefficient across a medium. The suggested parametric extraction method falls in the category of the resonator-based microwave detection methods. Although the resonator method is highly accurate, it is inherently narrowband and a separate measurement setup is required for each frequency. The resonator method typically involves the determination of the complex dielectric constant by measuring the resonance frequency and the resonance bandwidth of the microwave device that contains the dielectric sample. Some of the benefits of the proposed phase-based dielectric detection system are in order.

In the traditional detection systems, the resonance frequency (and hence the real part of the dielectric permittivity $\varepsilon_r$) is derived solely by observing the dip (or rise) in the amplitude characteristics. In the present invention, the double phase slope reversal provides an additional salient feature that can be detected in addition to the amplitude dip. Hence the ambiguity that may arise due to the auxiliary resonances (which occur due to material impurities or fabrication imperfections) may be reduced. Furthermore, the resonance bandwidth (or the Q-factor) calculation only requires the slope of the anomalous dispersive phase and the absolute phase measurements are not required. The bandwidth determination is, therefore, a two point measurement procedure (the resonance and another point for slope). On the other hand, the traditional amplitude-based detection system employs a three point measurement procedure where 'absolute' amplitude measurements are obtained at the resonance and two points on each side of the resonance. It may be noted that the dominant phase behavior results from the anomalous dispersive resonant circuit (see FIG. 1). The external circuit mostly affects the amplitude characteristics. Therefore, there is a less stringent requirement on the equipment calibration in the parametric detection system based on anomalous dispersion.

The present invention requires measurement of the slope of the anomalous phase which is a result of a very strong dispersion (see FIG. 6). Therefore, the measurement procedure is not drastically affected by the inaccuracies in the equipment. Moreover, in the proposed invention, there is no need to measure the absolute value of the phase, rather, the relative slop of the phase is only required. Therefore, the accuracy requirement of the equipment calibration is drastically reduced.

In an embodiment of the invention, the method invokes the Kramers-Kronig relationships that connect the real and imaginary parts of the complex dielectric constant. Hence only the slope of the anomalous phase is required to be measured for complete characterization of the real and the complex part of the dielectric constant of the sample under test.

In an embodiment of the invention, the same structure can be used to measure the dielectric constant at different frequencies just by changing the length of the stub (Ls) of the printed anomalous dispersive circuit. All the other parameters including the measurement setup can remain the same.

In an embodiment of the invention, the dielectric material that needs to be characterized is tailored mechanically in a rectangular shaped slab as shown in FIG. 6. The dimensions are comparable to the wavelength of an electromagnetic wave that propagates in the material. The rectangular slab is treated as a microwave substrate and a conductive copper strip along with an open circuit stub is printed on its one of the faces. The second face is covered with a conducting plane. In this configuration, the strip and the ground plane form a two-port micro-strip transmission line. The transmission line which comprises the strip and the stub have strip length "d", a strip width "W", a stub width "W" and a stub length "Ls". The substrate material has a length (d), a height (H) and a width larger than 5 W, preferably in the range of 6 W-7 W. The strip is preferably centered between the opposite sides of the substrate material such that at least a distance of 2 W is defined between the strip and each edge, preferably 2.5-3 W since the microwave signal through the ground plane spreads by 2-3 W at each side. The transmission phase (also known as S21 Phase) is measured between the two ports in a range of frequencies. In this specific micro-strip configuration, the transmission phase exhibits a unique 'reversal' in its slope. The frequency of the phase reversal is approximately the frequency at which the open circuit stub is half-wavelength long. This phenomenon of reversal of the transmission phase is termed as 'anomalous dispersion' and the phase is called 'anomalous phase'. Once the frequency and slope of the anomalous phase is determined, the real part of the dielectric constant (the relative permittivity) is given by the following equation:

$$\varepsilon_r = \frac{2\varepsilon_e \sqrt{1+12\frac{H}{W}} - \sqrt{1+12\frac{H}{W}} + 1}{1+\sqrt{1+12\frac{H}{W}}}$$

The imaginary part of the dielectric constant is determined by the following equation:

$$\varepsilon_i = \frac{2\varepsilon_r \alpha_d \sqrt{\varepsilon_e} (\varepsilon_r - 1)}{\beta \varepsilon_r (\varepsilon_e - 1)}$$

where $\alpha$ is the attenuation constant which can be calculated from the transmission phase slope by standard ABCD matrix technique, where $\beta_o$ is the free space phase constant, and where $\varepsilon_e$ is the effective dielectric constant given by:

$$\varepsilon_e = \frac{c^2}{16 L_s^2 f_o^2}$$

As a first aspect of the invention, as illustrated in FIG. 14, there is provided a method of determining a dielectric property associated with a substrate material, the method comprising:

obtaining transmission and reflection parameters for a transmission line connected to said substrate material over a specified frequency range;

determining a transmission phase response based on the transmission and reflection parameters;

determining an anomalous phase slope characterized by a double slope reversals based on the transmission phase response;

determining a resonance frequency based on a centre point of the anomalous phase slope reversals, where the center point corresponds to an anomalous phase at the resonance frequency; and determining the dielectric constant based on the resonance frequency, the anomalous phase at the resonance frequency and the anomalous phase slope.

The extraction method of determining the dielectric constant is a computer implemented method.

As a further aspect of the invention, as illustrated in FIG. 15, there is provided a dielectric constant analyzer device comprising a microprocessor or a microcomputer adapted to determine a dielectric property associated with a substrate material by:

measuring transmission and reflection parameters for a transmission line connected to said substrate material over a specified frequency range;

determining a transmission phase response based on the transmission and reflection parameters;

determining an anomalous phase slope characterized by a double slope reversals based on the transmission phase response;

determining a resonance frequency based on a centre point of the anomalous phase slope reversals, where the center point corresponds to an anomalous phase at the resonance frequency; and determining the dielectric constant based on the resonance frequency, the anomalous phase at the resonance frequency and the anomalous phase slope.

As another aspect of the invention, as illustrated in FIG. 16, there is provided a microprocessor or a microcomputer adapted to determine a dielectric property associated with a substrate material by:

obtaining transmission and reflection parameters for a transmission line connected to said substrate material over a specified frequency range;

determining a transmission phase response based on the transmission and reflection parameters;

determining an anomalous phase slope characterized by a double slope reversals based on the transmission phase response;

determining a resonance frequency based on a centre point of the anomalous phase slope reversals, where the center point corresponds to an anomalous phase at the resonance frequency; and determining the dielectric constant based on the resonance frequency, the anomalous phase at the resonance frequency and the anomalous phase slope.

As a further aspect of the invention, there is provided a computer readable medium comprising computer executable instructions which when executed over a computer are adapted to determine a dielectric property associated with a substrate material by:

obtaining transmission and reflection parameters for a transmission line connected to said substrate material over a specified frequency range;

determining a transmission phase response based on the transmission and reflection parameters;

determining an anomalous phase slope characterized by a double slope reversals based on the transmission phase response;

determining a resonance frequency based on a centre point of the anomalous phase slope reversals, where the center point corresponds to an anomalous phase at the resonance frequency; and determining the dielectric constant based on the resonance frequency, the anomalous phase at the resonance frequency and the anomalous phase slope.

Preferably, the transmission and reflection parameters are obtained from ABCD or scattering parameters (s-parameters).

Preferably, determining the dielectric constant comprises determining a real part of the dielectric constant using the resonance frequency and the anomalous phase at the resonance frequency, and determining an imaginary part of the dielectric constant using the anomalous phase slope. Preferably, the real part of the dielectric constant is determined first and the imaginary part is determined second.

Preferably, the material is a solid material. However, the material can also be a fluid material, preferably liquid.

Preferably, frequency range comprises a frequency range in the vicinity of the resonance frequency of the substrate material.

Preferably, the transmission line comprises a conductive strip having a strip width and a strip length and a stub extending perpendicularly from the conductive strip for forming an open circuit having a stub width and a stub length, the conductive strip having a first end adapted to be connected to a transmitter and a second end adapted to be connected to a receiver.

Preferably, the substrate material is adapted to be embedded in a resonant circuit comprising the transmitter and the receiver, where the substrate material is in the form of a slab treated as a microwave substrate and the transmission line is printed on a first face of the slab, where a second face of the slab is covered with a conducting plane to form a ground plane such that the transmission line and the ground plane form a two-port transmission line.

Preferably, the slab has a rectangular shape.

BRIEF DESCRIPTION OF THE DRAWINGS

The advantages and features of the present disclosure will become better understood with reference to the following detailed description and claims taken in conjunction with the accompanying drawing, in which:

FIG. 2(*b*) illustrates an implementation of series RLC resonator as an open-circuited stub.

FIG. 10(*b*) Illustrates the reconstructed amplitude responses of the microstrip model of FIG. 6. The plots are reconstructed by using the extracted dielectric constants that were found in previous sub-section and are plotted in FIGS. 8 and 9.

FIG. 15 illustrates an analyzer device in accordance with an embodiment of the invention.

FIG. 16 illustrates a microcomputer in accordance with an embodiment of the invention.

DETAILED DESCRIPTION OF THE INVENTION

The Anomalous Dispersive Circuit

A. Microwave Circuit Analysis of the Series RLC Circuit

Figure 1:
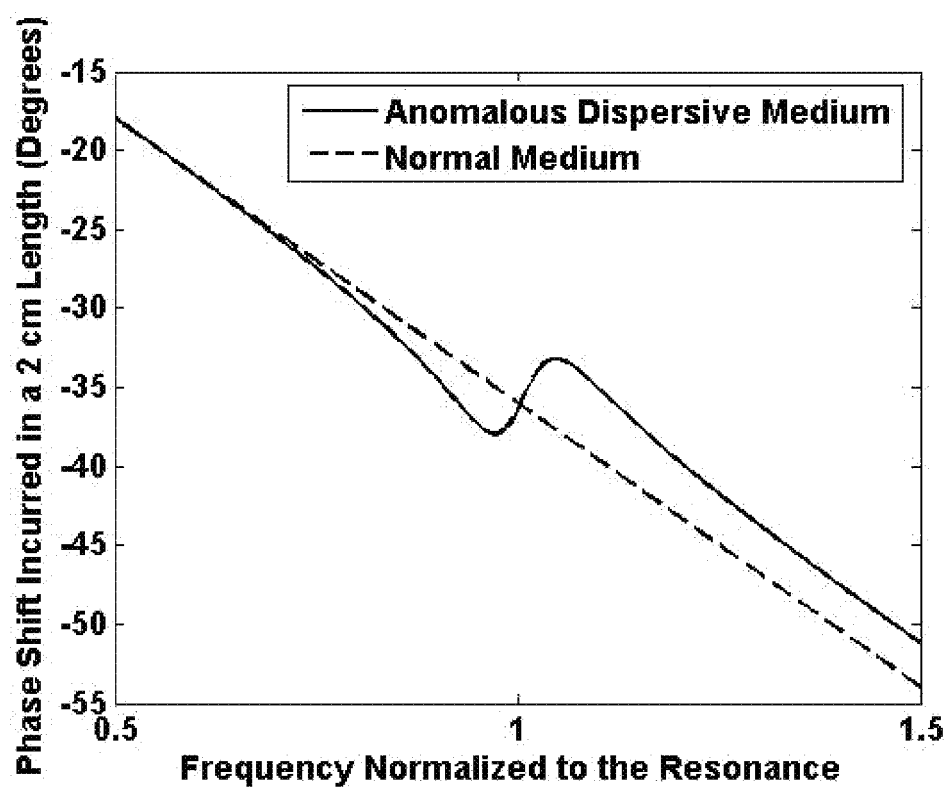
FIG. 1 illustrates a transmission phase across a medium undergoing the anomalous dispersion compared to the normal phase behavior.
Figure 2A:
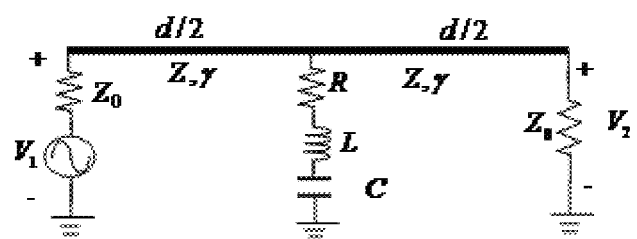
FIG. 2(*a*) illustrates a series RLC loaded transmission line circuit which shows anomalous dispersive effects.
Figure 2B:
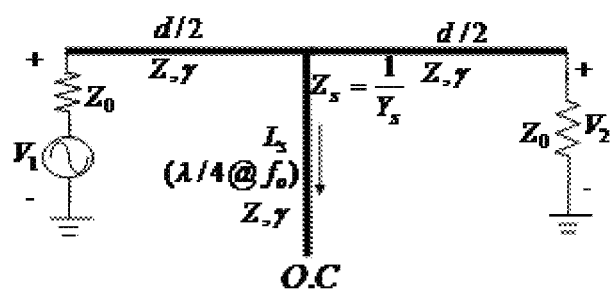

A parallel RLC resonator circuit which demonstrates the anomalous dispersion is analyzed using microwave circuit analysis. In particular, the effect of the dielectric changes on the transmission phase characteristics is studied. It is shown that the change in the real part of the complex permittivity changes the resonance frequency. The change in imaginary part (tan δ), however, affects the slope of the anomalous phase. Moreover, the effects of external circuit on the phase behavior are also shown. A parallel RLC resonator which is connected in series with the rest of the circuit exhibits anomalous dispersion characteristics within its resonance band. Alternatively, the dual of this circuit i.e. a series RLC resonator (FIG. 2a) will also demonstrate the anomalous dispersive behavior, if connected in parallel. the benefit of the latter configuration is its simpler realization in the microwave frequencies as an open-circuited quarter-wavelength stub (FIG. 2b) that loads a host transmission line of impedance Z. by a simple circuit analysis of FIG. 2b, the elements of the forward transmission matrix can be written as:

$$A = D = \cosh\gamma d + \frac{ZY_S}{2}\sinh\gamma d \quad \quad 1$$

$$B = Z\sinh\gamma d - Z^2 Y_S \sinh^2\frac{\gamma}{2} \quad \quad 2$$

$$C = \frac{1}{Z}\sinh\gamma d + Y_S^2 \cosh^2\frac{\gamma d}{2} \quad \quad 3$$

The complex propagation constant of the host transmission line can be written as:

$$\gamma = \alpha + j\beta_o \sqrt{\varepsilon} \quad \quad 4$$

where $\beta_o$ is the free space phase constant. $\alpha$ and $\varepsilon$ are the effective permittivity and attenuation constant of the host transmission line, respectively. $Y_s$ is the input admittance of the open circuited stub, given by:

$$Y_S = \frac{1}{Z}\frac{\tanh\alpha L_S + j\tan\beta_o \sqrt{\varepsilon} L_S}{1 + j\tan\beta_o \sqrt{\varepsilon} L_S \tanh\alpha L_S} \quad \quad 5$$

Figure 3:
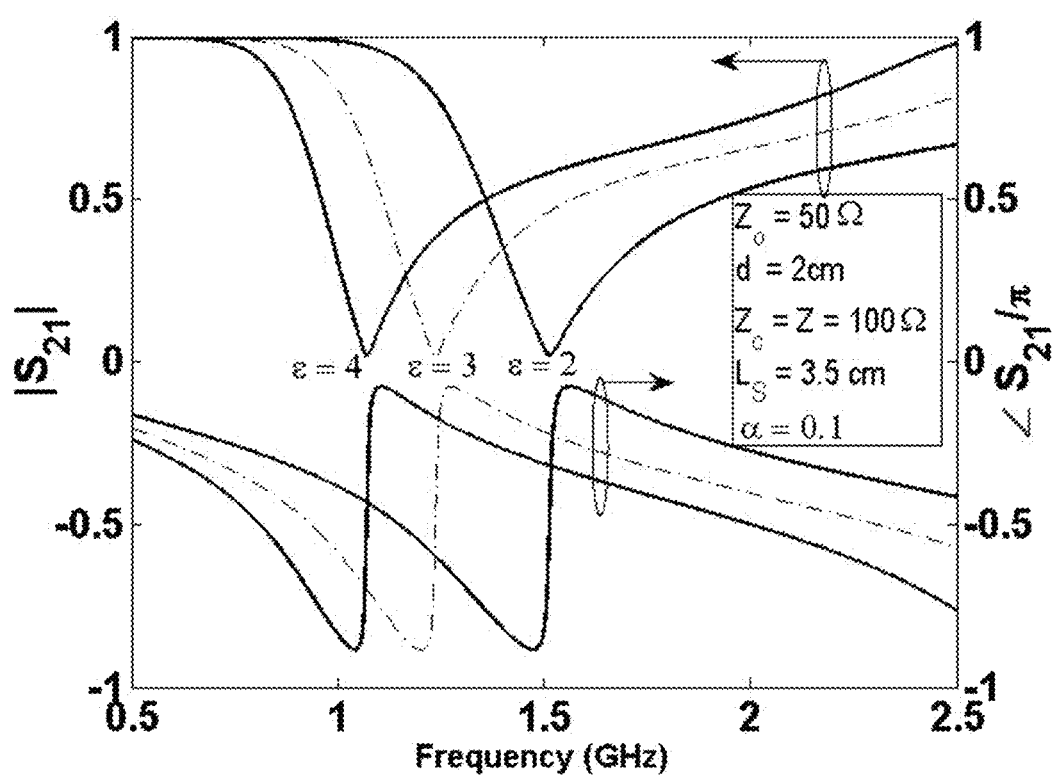
FIG. 3 illustrates a magnitude and phase responses of the anomalous dispersive circuit of FIG. 2*b*. The inset shows the circuit parameters used in the calculations.

The transmission coefficient can be written as follows after manipulating the modified Kirchhoff's current equation at the input and output:

$$S_{21} = \frac{2Z_o}{2AZ_o + \frac{A^2 Z_o^2}{B} + B - \frac{Z_o^2}{B}} \quad \quad 6$$

where $Z_o$ is the reference impedance of the measurement system. Consider the magnitude and phase plots given in FIG. 3 that are generated by solving (6) for representative circuit parameters (given in the figure's inset). The anomalous dispersion region is identified by the drop in the magnitude and reversal of the slope of the transmission phase. As the relative permittivity of the open-circuited stub is changed, the center of the anomalous dispersion region also shifts to the new resonant frequency $f_o$ which can be theoretically evaluated by assuming the term $\beta_o \sqrt{\varepsilon_s} L_s$ equal to $\pi/2$ in (4):

$$f_o = \frac{c}{4L_S \sqrt{\varepsilon}} \quad \quad 7$$

At the resonance frequency, the slope of the transmission phase curve is given by:

$$\frac{d \angle S_{21}}{df} = -\tan^{-1}\frac{\text{Im}\left(2AZ_o + \frac{A^2 Z_o^2}{B} + B - \frac{Z_o^2}{B}\right)}{\text{Re}\left(2AZ_o + \frac{A^2 Z_o^2}{B} + B - \frac{Z_o^2}{B}\right)} \quad \quad 8$$

Figure 4:
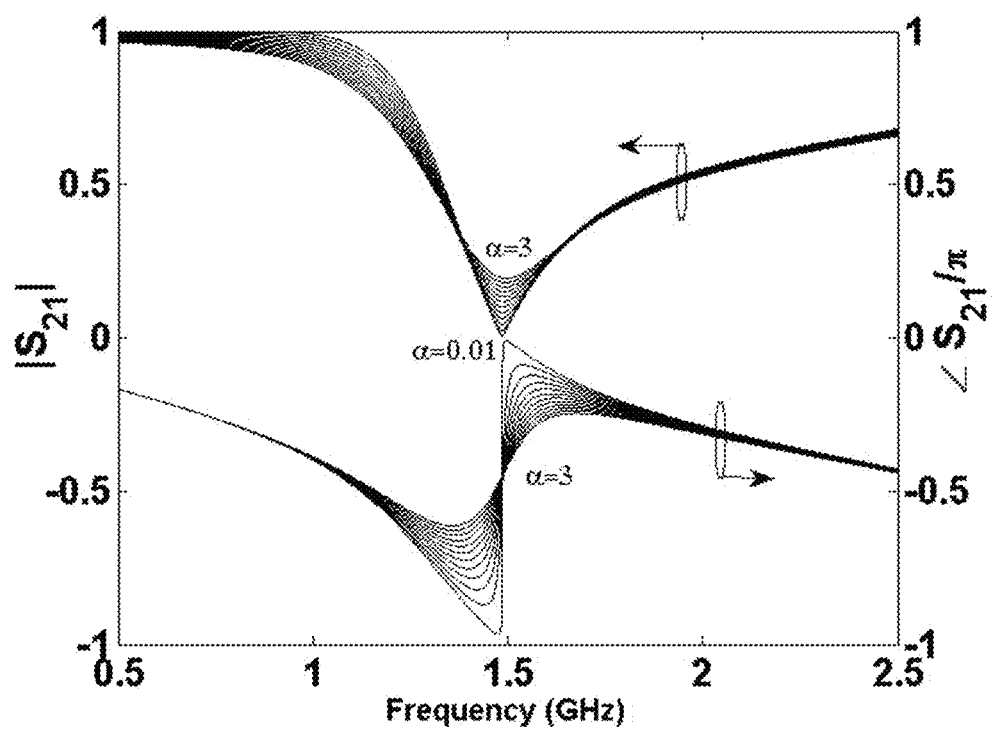
FIG. 4 illustrates a magnitude and phase responses of the anomalous dispersive circuit of FIG. 1*b* when the attenuation in the open-circuit stub is varied from $\alpha=0.01$ to $\alpha=3$.

B. The Overview of the Dielectric Detection Based on the Kramer-Kronig Relations In the circuit under study, the slope to attenuation relationship of the transmission phase curve (which will be further referred to as anomalous phase) can be understood by referring to FIGS. 2 (a) and (b) and observing that the lower resistance R (and hence lower attenuation constant α) corresponds to lower output voltages, thus leading to more attenuation in the circuit. Consequently, as depicted in FIG. 4, the slope of the anomalous phase increases with the decrease in the attenuation constant of the open-stub. The slope to attenuation relation also gives an indication to the correspondence between the three resonator parameters, namely: the quality factor (Q-factor), the slope of the anomalous phase and the bandwidth of the series resonator. With the decrease in the losses, the Q-factor increases leading to the increase of the phase-slope. Therefore, by detecting the slope of the anomalous phase, the attenuation in the stub can be estimated.

It may be noted that this strong connection between the magnitude and the anomalous phase is the consequence of the Kramers-Kronig relation which links the real and imaginary part of the complex wave propagation constant. The circuit interpretation of the Kramer-Kronig relation enables us to determine the dielectric behavior of the host medium by either the magnitude or the phase response. The Kramer-Kronig relation for the anomalous dispersive circuit can be further illustrated by writing (6) in terms of magnitude and phase under the small transmission line approximation (d<<λ):

$$|S_{21}| = \frac{2/Z_o Z}{\left(\frac{2}{ZZ_o} - \frac{Y_i\theta}{Z_o} - \frac{Y_iY_r\theta}{2} - \frac{Y_r}{Z}\right) +} \quad (9)$$
$$j\left(\frac{Y_r\theta}{Z_o} + \frac{Y_r^2\theta}{4} - \frac{Y_i^2\theta}{4} + \frac{Y_i}{Z} + \frac{\theta}{Z_o^2}\right)$$

$$\angle S_{21} = -\tan^{-1}\left(\frac{\frac{Y_r\theta}{Z_o} + \frac{Y_r^2\theta}{4} - \frac{Y_i^2\theta}{4} + \frac{Y_i}{Z} + \frac{\theta}{Z_o^2}}{\frac{2}{ZZ_o} - \frac{Y_i\theta}{Z_o} - \frac{Y_iY_r\theta}{2} - \frac{Y_r}{Z}}\right) \quad (10)$$

where $\theta = \beta_o\sqrt{\varepsilon}d$ and $Y_r$ and $Y_i$ are the real and imaginary parts of the open-circuit admittance. Both the magnitude and phase are the functions of frequency ($\omega$), the relative permittivity ($\varepsilon$) and the attenuation constant ($\alpha$). Hence if the frequency is known, a dielectric material can be completely characterized by the knowledge of either the phase or the magnitude. The dielectric characterization procedure discussed here utilizes double phase-slope reversal around the resonance to measure the resonant frequency of the circuit.

Hence, the detector in this case determines the slope of the phase response and locks on the frequency band which is in between two phase slope reversals. Once the resonance and the slope are determined, the permittivity and the attenuation parameters can then be calculated by solving (1)-(5) and (8).

C. The Less-stringent Calibration Requirement

Figure 5:
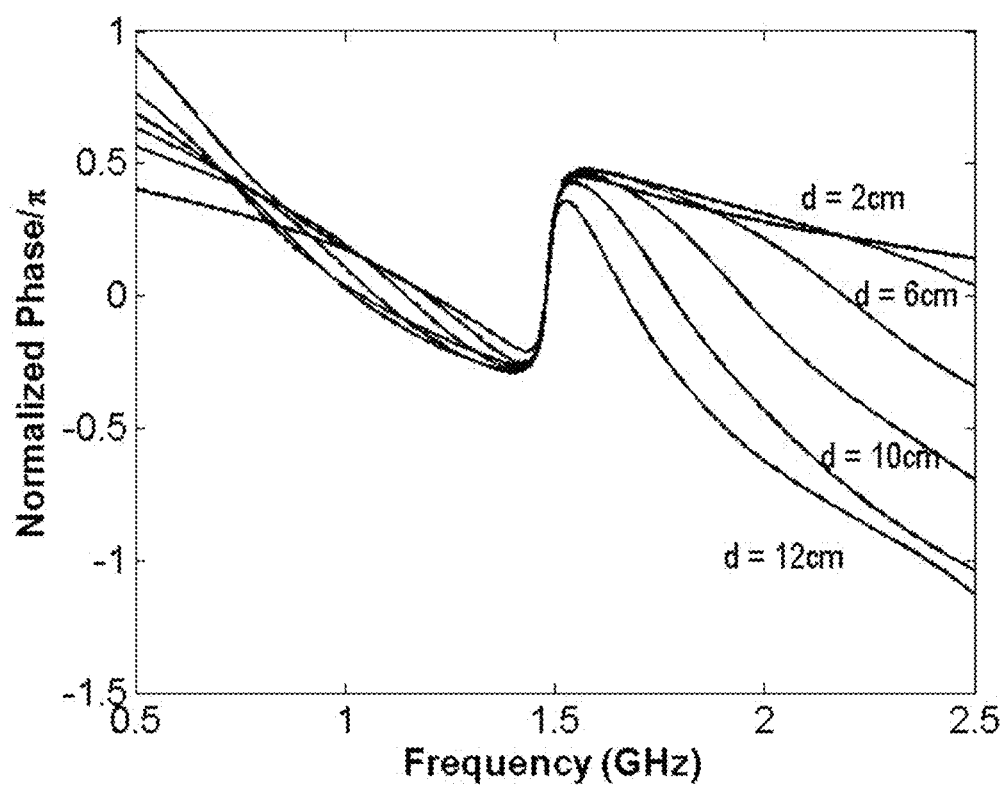
FIG. 5 illustrates the fact that the transmission phase in the anomalous dispersion band strongly depends on the open-circuit stub's geometry

Other resonance-based dielectric characterization techniques rely on the absolute magnitude measurement which requires accurate calibrations of the external circuitry. The proposed technique, on the other hand, calculates the phase slope by measuring two points on the anomalous phase without requiring the measurement of the absolute phase. Moreover, since the phase slope in the anomalous dispersion region depends strongly on the open-circuited stub geometry; and the relevance to the external circuit parameters is minimal. This phenomenon can be observed by noticing no change in the location and slope of the anomalous phase when the length of the host transmission line is varied (FIG. 5). Therefore, the errors arising due to calibration and the inaccuracies in the external circuitry are suppressed in the proposed technique.

III. Parameters Retrieval of Microwave Substrates (Simulation Results)

A. The Complex Dielectric Constant Retrieval

The present section illustrates the extraction of the complex permittivity from the transmission phase characteristics of dielectric used as a substrate in a microstrip based anomalous dispersive circuit. The extracted dielectric permittivity is used to reconstruct the amplitude and phase spectrum for a wide range of spectrum. The complex dielectric constant (or the relative permittivity) of a dielectric material is written as $\varepsilon_r(1+j\tan\delta)$, where the loss tangent is the ratio of the imaginary part to the real part. In this sub-section, we show the both the components of the complex permittivity can be extracted by utilizing the dielectric as a substrate for the printed anomalous dispersive circuit. Consider the schematic diagram (FIG. 5) of the proposed microstrip model, implemented in the microwave circuit simulator Agilent's Advanced Design System (ADS). The dielectric losses are assumed to vary in accordance with the Svensson-Djordjevic model (by fixing the reference loss tangent of the substrate at 0.01 at a frequency of 1.45 GHz).

Figure 7:
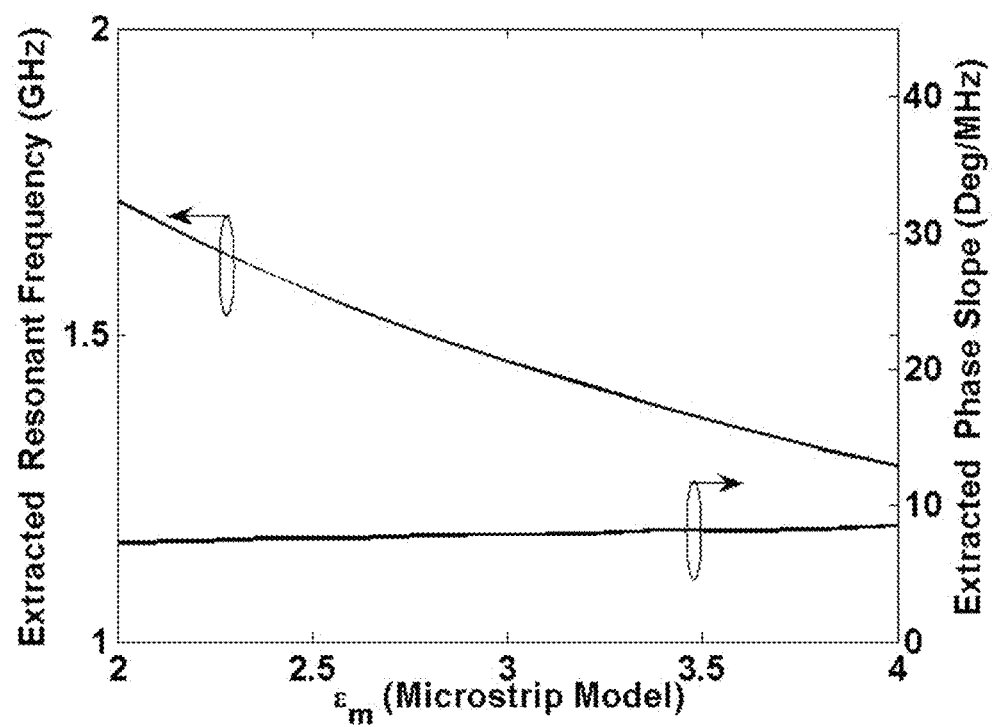
FIG. 7 illustrates the extracted resonant frequencies and the phase slopes as functions of dielectric constant of the microstrip model.

To demonstrate the parameter extraction of sample dielectrics, the real part of the dielectric constant of the ADS microstrip model ($\varepsilon_m$) is varied from 2 to 4 and the frequency versus transmission-phase plots are obtained for each case. The parametric extraction consists of first extracting the resonant frequency $f_o$ and the slope of the anomalous phase in its vicinity. This is done by measuring the phase value at in the region bounded by the two consecutive phase slope reversals and an additional off-resonance phase reading. For the variable permittivity microstrip model considered here, the extracted resonant frequencies and the corresponding phase-slopes are plotted in FIG. 7 as functions of increasing substrate's relative permittivity. The relevance between the change in the relative permittivity and its effect on the resonant frequency and the anomalous phase-slopes is similar to the one observed in the transmission line model analysis of FIG. 3. From the resonance frequencies, the effective dielectric constant of the dielectric that hosts the open-stub can be calculated by applying (7):

$$\varepsilon_e = \frac{c^2}{16L_s^2 f_o^2} \quad (11)$$

Once the effective permittivity is determined, the real part of the dielectric constant ($\varepsilon_r$) and the characteristic impedance of the host transmission line can be calculated by using the well known analytical riles:

$$\varepsilon_r = \frac{2\varepsilon_e\sqrt{1+12\frac{H}{W}} - \sqrt{1+12\frac{H}{W}} + 1}{1+\sqrt{1+12\frac{H}{W}}} \quad (12)$$

$$Z = \begin{cases} \frac{60}{\sqrt{\varepsilon_e}}\ln\left(\frac{8d}{W} + \frac{W}{4H}\right), \text{ for } W/H \leq 1 \\ \frac{120\pi}{\sqrt{\varepsilon_e}\left[\frac{W}{H} + 1.393 + 0.667\ln\left(\frac{W}{H} + 1.444\right)\right]}, \text{ for } W/H \geq 1 \end{cases} \quad (13)$$

Finally, the effective attenuation constant is evaluated by numerically solving (1)-(6), (8) and (10)-(12). A plot of the extracted parameters as functions of the microstrip model permittivity ($\varepsilon_m$) is given in FIG. 8. A very close match can be observed between the extracted parameters and the pre-fixed model parameters, showing the validity of the extraction procedure. The minor differences between the model and extracted parameters are because of the analytical approximations assumed in deriving (11) and (12). There is a slight increase in the modeled and extracted attenuation constant with the permittivity indicates its dependence on the frequency according to the Svensson-Djordjevic dielectric model.

Figure 8:
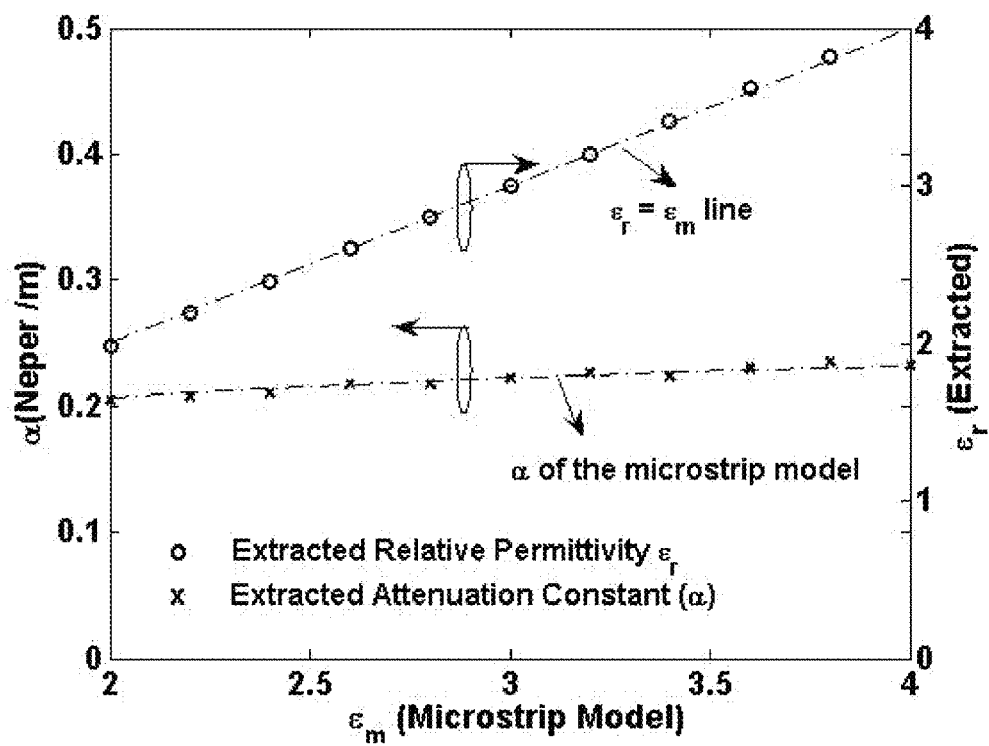
FIG. 8 illustrates the comparison extracted relative permittivity and attenuation constants compared with the prefixed model parameters.
Figure 9:
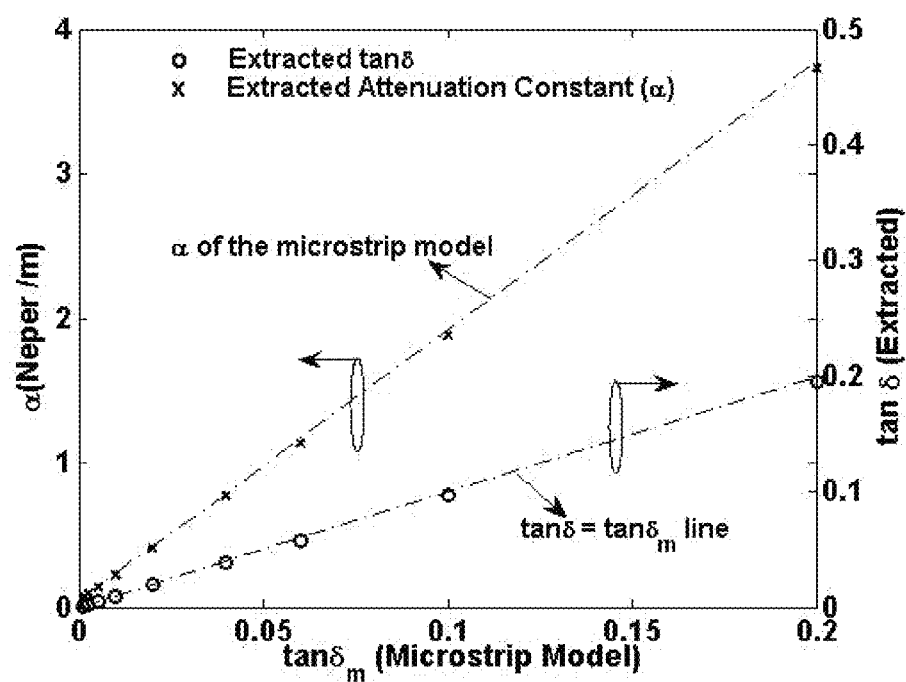
FIG. 9 illustrates the comparison extracted loss tangents and attenuation constants compared with the prefixed model parameters.

Next the dielectric constant of the microstrip model ($\varepsilon_m$) is fixed at 2.93 and the reference loss-tangent (tan $\delta_m$) is varied from 0.001 to 0.2. The extracted values of the effective attenuation constant and the loss tangents determined from the phase curves and are shown in FIG. 8. The dielectric attenuation constant $\alpha_d$ can be separated from the total attenuation ($\alpha$) by subtracting the attenuation constant due to the conductor losses, given by:

$$\alpha_c = \frac{R_s}{ZW} \quad (13)$$

Where $R_S=\sqrt{2\pi f_o\mu_o/2\sigma}$ is the surface resistivity of the conductor. The loss tangent can then be calculated by using the microstrip rule:

$$\tan\delta_e = \frac{2\alpha_d\sqrt{\varepsilon}(\varepsilon_e-1)}{\beta_o\varepsilon_e(\varepsilon-1)} \qquad 14$$

B. Reconstruction of Phase and Amplitude Plots

Figure 10A:
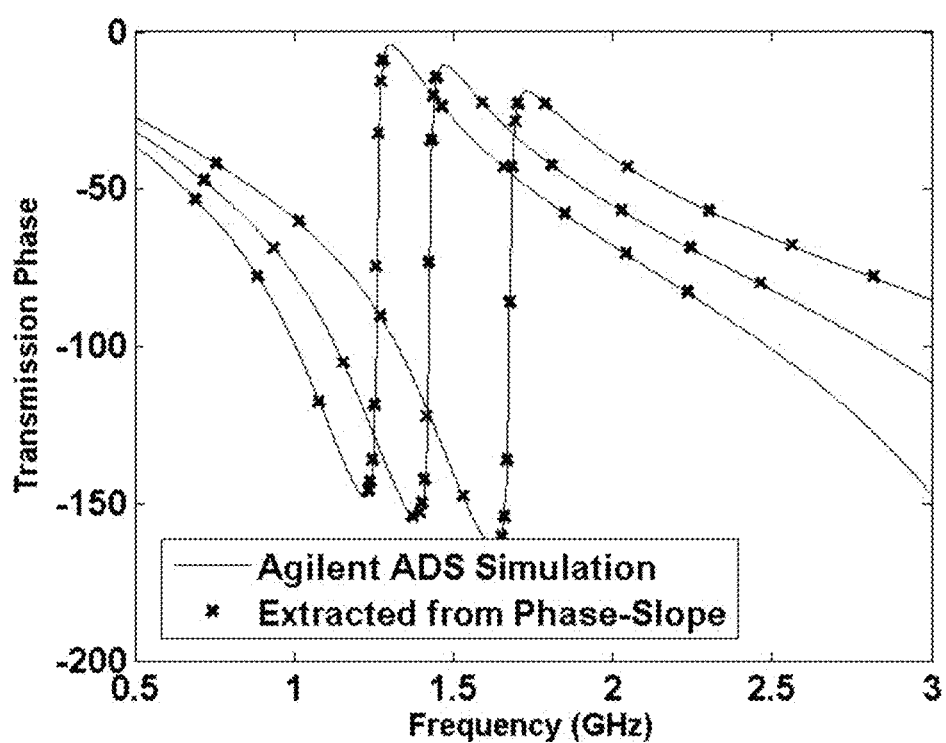
FIG. 10(*a*) illustrates the reconstructed Phase of the microstrip model of FIG. 6. The plots are reconstructed by using the extracted dielectric constants that were found in previous sub-section and are plotted in FIGS. 8 and 9.
Figure 10B:
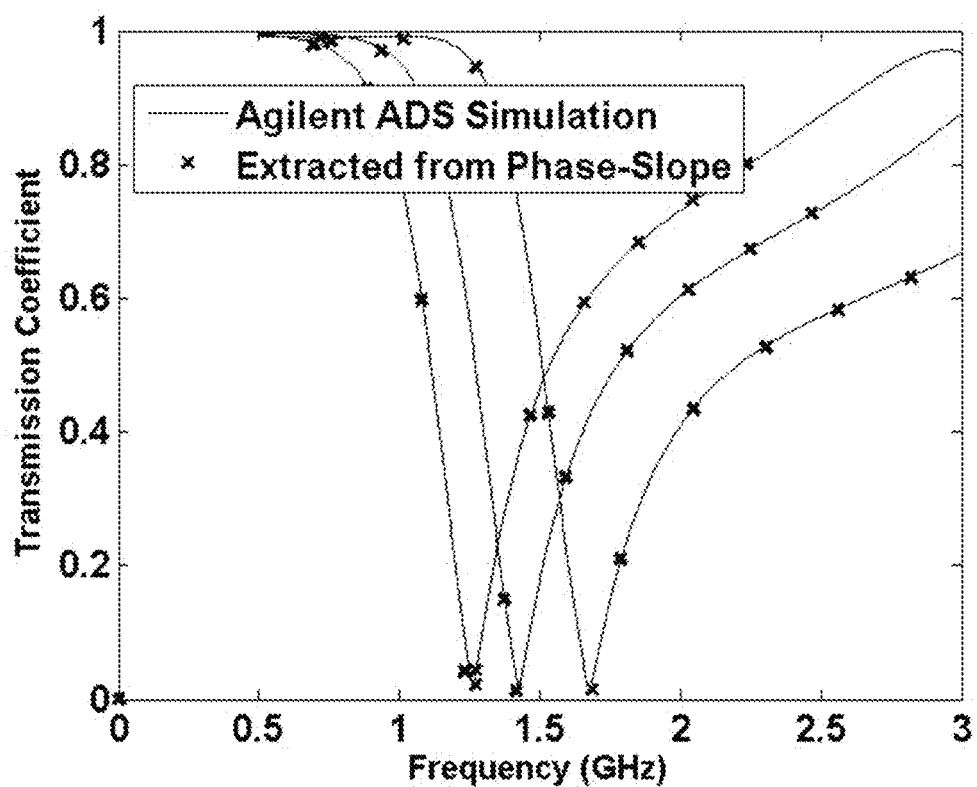

To show the validity of the fact that the material can be completely characterized from the slope of the anomalous dispersive phase, the amplitude and phase responses at other frequencies are reconstructed by applying the retrieved complex dielectric constant to (6). As shown in FIGS. 10 (a) and (b), the retrieved responses closely follow the ADS simulations. The close agreement between the model and the extracted curves and the fact that the amplitude responses here are obtained from the phase information also illustrate the legitimacy of the Kramer-Kronig relations.

IV. Parameters Retrieval of Microwave Substrates (Experimental Results)

In this section, parametric extraction is applied to five dielectric samples. The experimental results are close to the theoretical parameters.

A. Extraction of Complex Dielectric Constant

Figure 6:
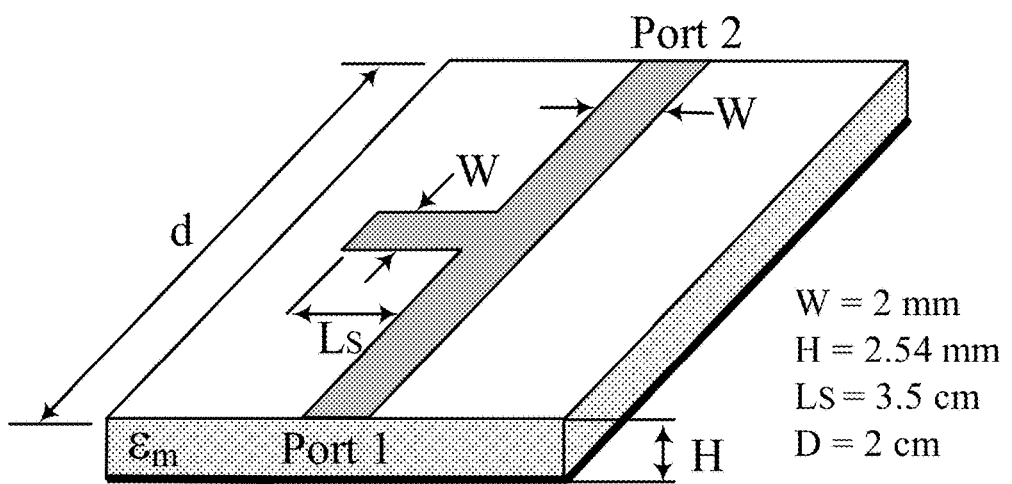
FIG. 6 illustrates a microstrip model to demonstrate the parameter retrieval of the substrate material with dimensions of W=2 mm, d=2 cm, Ls=3.5 cm.
Figure 11:
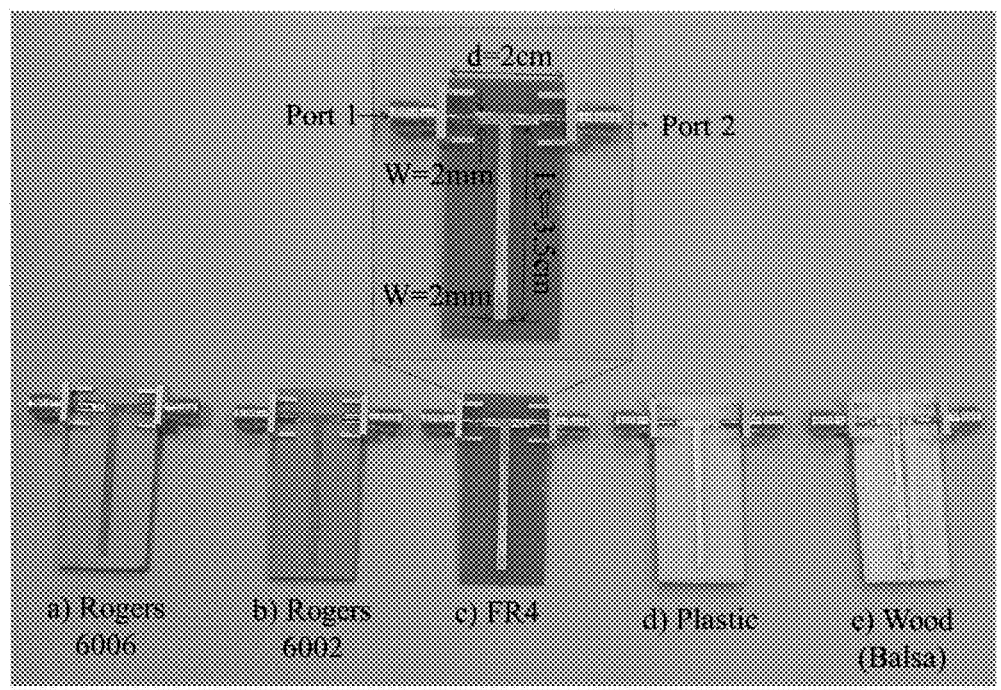
FIG. 11 illustrates the photograph of the five manufactured and measured samples on different substrate materials: a) Rogers6006 b) Rogers6002 c) FR4 d) Plastic e) Balsa wood with same microstrip dimensions of W=2 mm, d=2 cm, Ls=3.5 cm.

The parameter extraction method using the anomalous dispersion phase is applied practically to determine the dielectric parameters of five known dielectrics. A photograph of the samples is depicted in FIG. 11. The samples were prepared by printing microwave anomalous dispersion circuit of FIG. 6 on the relevant material. A summary of the sample parameters is provided in Table 1. The dielectric properties of materials provided by Rogers™ are calibrated at 10 GHz. The transmission characteristics (S21 magnitude and phase) are determined by the Rohde & Schwarz, ZVL13 Vector Network Analyzer device. Note that the only measurement needed for the parameter extraction is the transmission phase in the anomalous dispersive region. The transmission magnitude is determined to compare the transmission characteristics reconstructed from the extracted parameters.

Two critical parameters in the determination of the complex dielectric constant are the resonant frequency and the slope of the anomalous dispersion phase. The resonant frequency is extracted from the S21 phase by detecting the center point of the two phase reversals in anomalous dispersion band. The relative permittivity is found by applying (11). Finally, the relations (12)-(14) are used to extract the attenuation constant and the loss tangent after finding the slope of the anomalous phase. The extracted parameters are tabulated in Table 2. The relative permittivities of the first four samples in Table 2 are found to be within 10% error of the actual material. The maximum error (8%) is found in the case of FR4 whose electrical parameters are known to fluctuate rapidly after 1 GHz. Note that the dielectric losses as indicated by the loss tangents are over determined compared to the actual ones. This apparent discrepancy is due to the radiation losses from the-wave length which are not accounted for in the microstrip model. The discrepancy can be considerably reduced by fabricating the anomalous dispersive circuit in a stripline environment in which radiation losses are negligible.

B. Reconstruction of Phase and Magnitude Responses

Figure 12:
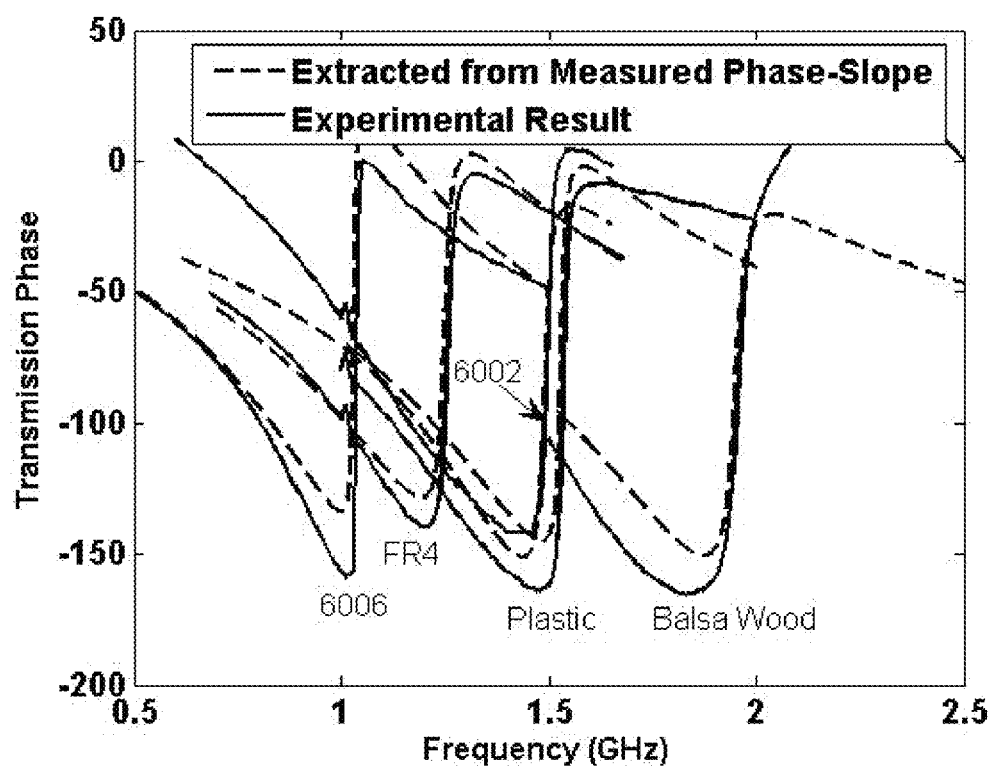
FIG. 12 illustrates the measured and reconstructed phase responses of different microstrip dielectric samples. The phase response is reconstructed from the extracted dielectric constants (provided in Table 2).
Figure 13:
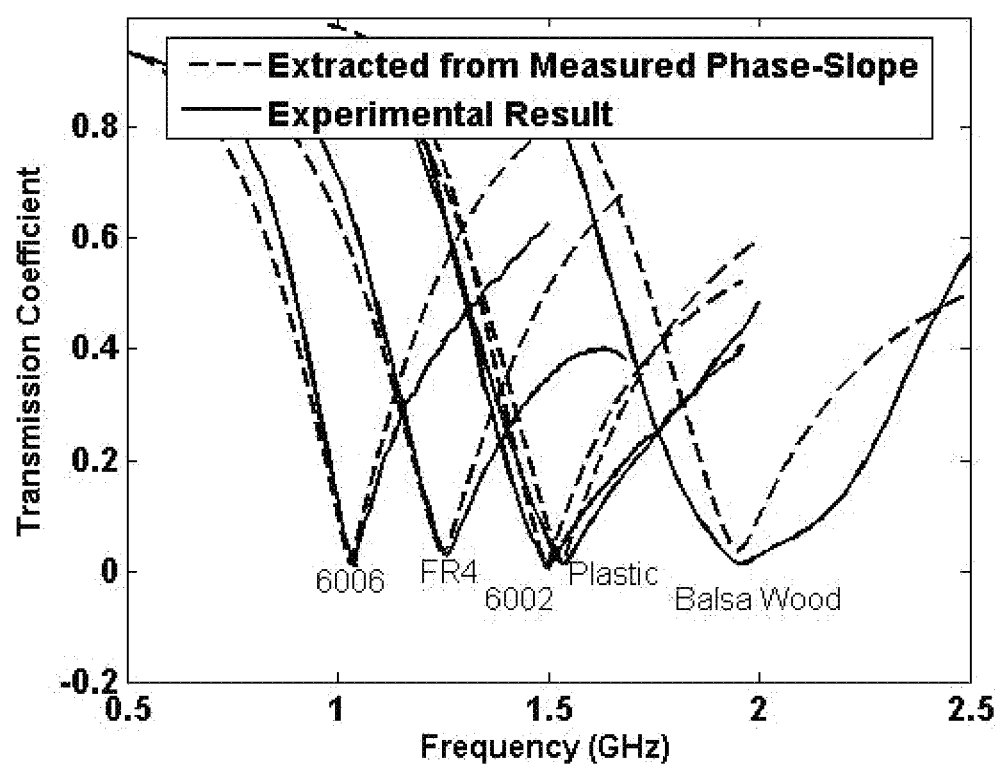
FIG. 13 illustrates the measured and extracted amplitude responses of different microstrip dielectric samples (provided in Table 2)
Figure 14:
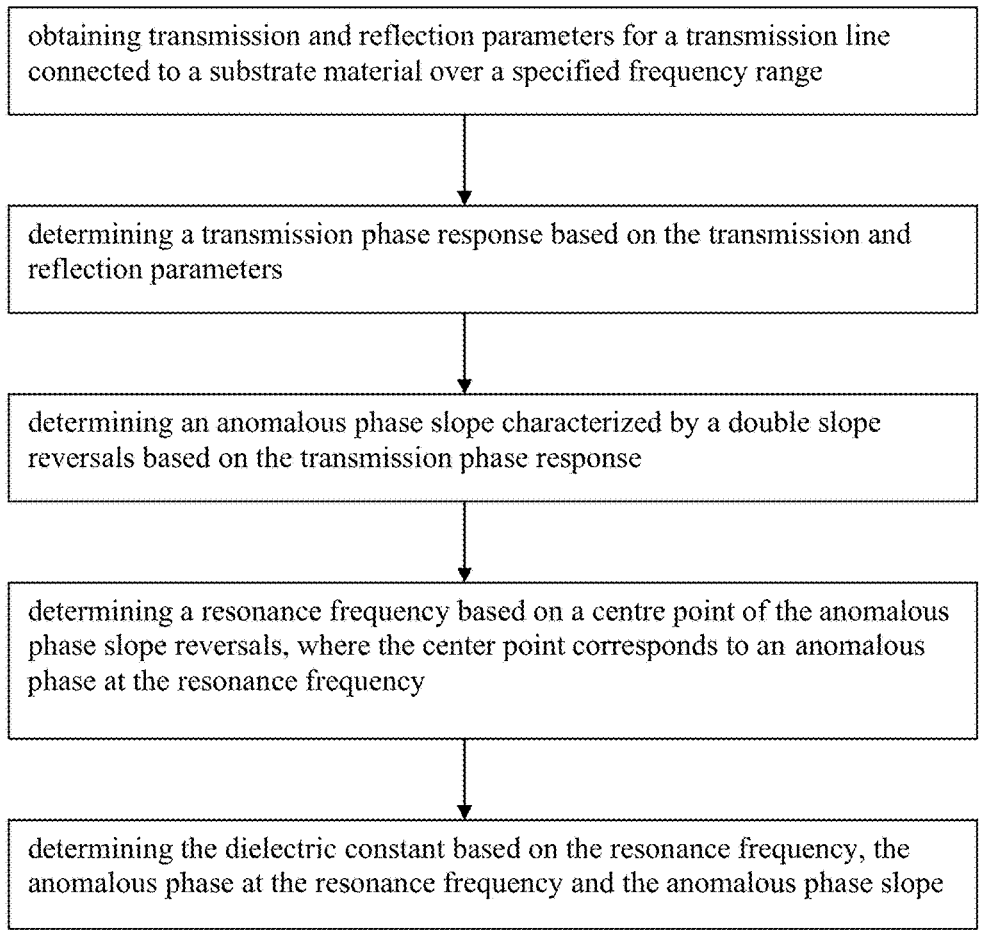
FIG. 14 illustrates a method of determining the dielectric constant of a material in accordance of an embodiment of the invention.

To validate the parametric extraction method, the transmission phase and magnitude plots are reconstructed (in simulation) by employing the extracted dielectric constant in (6). As shown in FIGS. 12 and 13, a very close agreement with the experimental curves in the vicinity of the anomalous dispersion region is obtained. Away from the anomalous dispersion region, the difference between the measured and reconstructed transmission phase is mainly due to the fabrication imperfections and errors in the calibration process which does not include the effect of the SMA connectors. The magnitude response of the Balsa wood has a wider resonant bandwidth due to its inhomogeneous composition and the presence of moisture.

TABLE 1

Samples' Parameters

| Material | $\varepsilon_r$ | $\tan\delta$ | Thickness (H) |
|---|---|---|---|
| Rogers 6002 | 2.94 | 0.0012 | 2.54 mm |
| Rogers 6006 | 6.15 | 0.0027 | 1.91 mm |
| FR4 | 4.34 (1 GHz) | 0.017 (1 GHz) | 1.5 mm |
| Balsa Wood | 1.37 (1 MHz) | 0.012 (1 MHz) | 1.5 mm |
| Plastic | 2-4 | Wide range | 1.5 mm |

TABLE 2

Extracted Parameters

| Material | Resonant Frequency | Phase Slope | $\varepsilon_r$ | $\tan\delta$ |
|---|---|---|---|---|
| Rogers 6002 | 1.49 GHz | 4.6 deg/MHz | 2.8 | 0.0026 |
| Rogers 6006 | 1.05 GHz | 12.8 deg/MHz | 6.22 | 0.0057 |
| FR4 | 1.27 GHz | 4.2 deg/MHz | 4 | 0.02 |
| Wood | 1.98 GHz | 2.93 deg/MHz | 1.31 | 0.0226 |
| Plastic | 1.55 GHz | 6.72 deg/MHz | 2.48 | 0.01 |

The present invention presents among others a novel dielectric characterization method based on measuring transmission phase of a material undergoing anomalous dispersion. The material sample is subjected to the anomalous dispersion by utilizing it as a substrate on which an open-circuited half-wavelength (which mimics a series RLC resonator) is printed. The real part of the dielectric constant (relative permittivity $\varepsilon_r$) is extracted from the anomalous dispersion resonance and the loss tangent (tan δ) is derived from the slope of the anomalous dispersive phase. In this way, as dictated by the Kramer-Kronig relations, the transmission phase across the dielectric can completely characterized its electrical properties. The proposed method is superior to the contemporary resonator-based dielectric characterization methods in several ways. These methods mostly rely on 'absolute' amplitude measurements which are affected by external circuitry of the measuring equipment and require fine calibrations. The proposed method, however, derives the dielectric parameters from the phase characteristics in the anomalous dispersive spectrum which is independent of external circuitry. Hence only 'relative' phase measurements are needed and the calibration requirements are less strict. Furthermore, the Q-factor (or resonator bandwidth) in the suggested technique can be estimated by measuring the phase slope thus requiring only two phase measurements. The amplitude-based methods, on the other hand, calculate the bandwidth by taking several measurements around the resonance frequency.

The proposed method is applied to determine complex dielectric constants of five material samples. A close agreement is observed between the extracted and known dielectric constants. Furthermore, the phase and amplitude responses within and outside the anomalous dispersion region are reconstructed by employing extracted parameters in the analytical circuit equations. The reconstructed transmission characteristics follow the measured results in a close manner, which validates the notion supported by the Kramer-Kronig relations.

The foregoing descriptions of specific embodiments of the present invention have been presented for purposes of illustration and description. They are not intended to be exhaustive or to limit the present invention to the precise forms disclosed, and obviously many modifications and variations are possible in light of the above teaching. The embodiments were chosen and described in order to best explain the principles of the present invention and its practical application, and to thereby enable others skilled in the art to best utilize the present invention and various embodiments with various modifications as are suited to the particular use contemplated. It is understood that various omissions and substitutions of equivalents are contemplated as circumstances may suggest or render expedient, but such omissions and substitutions are intended to cover the application or implementation without departing from the spirit or scope of the present invention.

The invention claimed is:

1. A method of determining a dielectric property associated with a substrate material, the method comprising:
   printing an anomalous dispersive circuit on the substrate material;
   connecting a transmission line to the substrate material;
   obtaining transmission and reflection parameters for the transmission line connected to said substrate material over a specified frequency range, wherein the transmission line comprises a conductive strip having a first end connected to a transmitter and a second end connected to a receiver;
   determining a transmission phase response based on the transmission and reflection parameters;
   determining an anomalous phase slope characterized by a double slope reversals based on the transmission phase response;
   determining a resonance frequency based on a centre point of the anomalous phase slope reversals, where the center point corresponds to an anomalous phase at the resonance frequency;
   determining the dielectric constant based on the resonance frequency, the anomalous phase at the resonance frequency and the anomalous phase slope, and
   applying the method of determining the dielectric constant based on the resonance frequency, the anomalous phase at the resonance frequency and the anomalous phase slope for calculating dielectric parameters of known dielectric materials;
      wherein the calculated dielectric parameters are within 10% error of actual dielectric parameters of the known dielectric materials;
      wherein the substrate material is tailored mechanically in the form of a rectangular shaped slab which is treated as a microwave substrate and the transmission line is printed on a first face of the rectangular shaped slab, and
      wherein a second face of the rectangular shaped slab is covered with a conducting plane to form a ground plane.

2. The method of claim 1, wherein the transmission and reflection parameters are obtained from ABCD or scattering parameters (s-parameters).

3. The method of claim 1, wherein determining the dielectric constant comprises determining a real part of the dielectric constant using the resonance frequency and the anomalous phase at the resonance frequency, and determining an imaginary part of the dielectric constant using the anomalous phase slope.

4. The method of claim 1 wherein the material is a solid material.

5. The method of claim 1, wherein the material is a fluid material.

6. The method of claim 1 wherein frequency range comprises a frequency range in the vicinity of the resonance frequency of the substrate material.

7. The method of claim 1 wherein the conductive strip of the transmission line has a strip width and a strip length and a stub extending perpendicularly from the conductive strip for forming an open circuit having a stub width and a stub length.

8. The method of claim 1, wherein the substrate material is adapted to be embedded in a resonant circuit comprising the transmitter and the receiver, and wherein the ground plane is formed such that the transmission line and the ground plane form a two-port transmission line.

9. A dielectric constant analyzer device adapted to determine a dielectric property associated with a substrate material by:
   printing an anomalous dispersive circuit on the substrate material;
   connecting a transmission line to the substrate material;
   measuring transmission and reflection parameters for the transmission line connected to said substrate material over a specified frequency range, wherein the transmission line comprises a conductive strip having a first end connected to a transmitter and a second end connected to a receiver;
   determining a transmission phase response based on the transmission and reflection parameters;
   determining an anomalous phase slope characterized by a double slope reversals based on the transmission phase response;
   determining a resonance frequency based on a centre point of the anomalous phase slope reversals, where the center point corresponds to an anomalous phase at the resonance frequency; and
   determining the dielectric constant based on the resonance frequency, the anomalous phase at the resonance frequency and the anomalous phase slope, and
   applying the method of determining the dielectric constant based on the resonance frequency, the anomalous phase at the resonance frequency and the anomalous phase slope for calculating dielectric parameters of known dielectric materials;
      wherein the calculated dielectric parameters are within 10% error of actual dielectric parameters of the known dielectric materials;
      wherein the substrate material is tailored mechanically in the form of a rectangular shaped slab which is treated as a microwave substrate and the transmission line is printed on a first face of the rectangular shaped slab, and
      wherein a second face of the rectangular shaped slab is covered with a conducting plane to form a ground plane.

10. The analyzer device of claim 9, wherein the transmission and reflection parameters are obtained from ABCD or scattering parameters (s-parameters).

11. The analyzer device of claim 9, wherein determining the dielectric constant comprises determining a real part of the dielectric constant using the resonance frequency and the anomalous phase at the resonance frequency, and determining an imaginary part of the dielectric constant using the anomalous phase slope.

12. The analyzer device of claim 9 wherein the material is a solid material.

13. The analyzer device of claim 9, wherein the material is a fluid material.

14. The analyzer device of claim 9 wherein frequency range comprises a frequency range in the vicinity of the resonance frequency of the substrate material.

15. The analyzer device of claim 9 wherein the conductive strip of the transmission line has a strip width and a strip length and a stub extending perpendicularly from the conductive strip for forming an open circuit having a stub width and a stub length.

16. The analyzer device of claim 9, wherein the substrate material is adapted to be embedded in a resonant circuit comprising the transmitter and the receiver, and wherein the ground plane is formed such that the transmission line and the ground plane form a two-port transmission line.

17. A microcomputer adapted to determine a dielectric property associated with a substrate material by:
    printing an anomalous dispersive circuit on the substrate material;
    connecting a transmission line to the substrate material;
    obtaining transmission and reflection parameters for the transmission line connected to said substrate material over a specified frequency range, wherein the transmission line comprises a conductive strip having a first end connected to a transmitter and a second end connected to a receiver;
    determining a transmission phase response based on the transmission and reflection parameters;
    determining an anomalous phase slope characterized by a double slope reversals based on the transmission phase response;
    determining a resonance frequency based on a centre point of the anomalous phase slope reversals, where the center point corresponds to an anomalous phase at the resonance frequency; and
    determining the dielectric constant based on the resonance frequency, the anomalous phase at the resonance frequency and the anomalous phase slope, and
    applying the method of determining the dielectric constant based on the resonance frequency, the anomalous phase at the resonance frequency and the anomalous phase slope for calculating dielectric parameters of known dielectric materials;
        wherein the calculated dielectric parameters are within 10% error of actual dielectric parameters of the known dielectric materials;
        wherein the substrate material is tailored mechanically in the form of a rectangular shaped slab which is treated as a microwave substrate and the transmission line is printed on a first face of the rectangular shaped slab, and
        wherein a second face of the rectangular shaped slab is covered with a conducting plane to form a ground plane.

18. The microcomputer of claim 17, wherein determining the dielectric constant comprises determining a real part of the dielectric constant using the resonance frequency and the anomalous phase at the resonance frequency, and determining an imaginary part of the dielectric constant using the anomalous phase slope.

* * * * *